United States Patent [19]

Wakita et al.

[11] Patent Number: 5,096,593

[45] Date of Patent: Mar. 17, 1992

[54] SEPARATION MATERIAL DERIVED FROM GLUCOMANNAN FOR BLOOD COAGULATION FACTOR, PREPARATION AND USE THEREOF

[75] Inventors: Masaaki Wakita; Takashi Tomoda; Masato Yamaguchi; Isao Joko; Hiroshi Morita, all of Tokyo; Tetsuro Yamamoto; Yoshiaki Motozato, both of Kumamoto, all of Japan

[73] Assignee: Kurita Water Industries Ltd., Tokyo, Japan

[21] Appl. No.: 631,735

[22] Filed: Dec. 18, 1990

[30] Foreign Application Priority Data

Dec. 21, 1989 [JP] Japan ................... 1-332321
Oct. 26, 1990 [JP] Japan ................... 2-290219

[51] Int. Cl.$^5$ .................................. B01D 15/08
[52] U.S. Cl. ........................... 210/656; 210/198.2; 210/502.1; 436/513; 436/529; 502/402; 502/404; 530/381; 530/383; 530/413
[58] Field of Search ............... 210/656, 198.2, 502.1, 210/691, 692; 502/402, 404; 530/381, 383, 413; 436/513, 519, 529

[56] References Cited

U.S. PATENT DOCUMENTS

| 4,675,385 | 6/1987 | Herring . |
| 4,882,426 | 11/1989 | Motozato ................... 536/114 |
| 4,883,598 | 11/1989 | Riethorst et al. ............ 210/656 |
| 4,948,814 | 8/1990 | Motozato et al. ............ 521/30 |

FOREIGN PATENT DOCUMENTS

| 0023607 | 11/1981 | European Pat. Off. . |
| 0179006 | 4/1986 | European Pat. Off. . |
| 0233620 | 8/1987 | European Pat. Off. . |
| 0303329 | 2/1989 | European Pat. Off. . |
| 60-136518 | 7/1985 | Japan . |
| 63-198632 | 8/1988 | Japan . |
| 64-13099 | 1/1989 | Japan . |
| 1-157000 | 6/1989 | Japan . |
| 1-221396 | 9/1989 | Japan . |

OTHER PUBLICATIONS

L. R. Snyder and J. J. Kirkland, "Introduction to Modern Liquid Chromatography", 2nd Ed., Wiley, New York (1979), pp. 192-195, 203.

*Primary Examiner*—Robert A. Dawson
*Assistant Examiner*—Sun Uk Lim
*Attorney, Agent, or Firm*—Flynn, Thiel, Boutell & Tanis

[57] ABSTRACT

The separation material for separating and recovering a blood coagulation factor comprises a porous matrix having linked thereon one or more ligands each consisting of a radical exhibiting an affinity for the blood coagulation factor to be recovered, said matrix having a specific surface area of at least 1.5 m$^2$ per milliliter of the separation material with respect to pores having diameters of at least 0.1 μm and being derived from a porous particulate material having an exclusion limit molecular weight of at least $1.5 \times 1^6$ as determined with polyethylene glycol. The separation material is prepared by the process steps of subjecting a porous particulate material having an exclusion limit molecular weight of at least $1.5 \times 10^6$ to activation by 1,1'-carbonyldiimidazolating, tresylating, carbodiimidizing, thiopropylating, epoxidizing, bromocyanizing or formylating using the corresponding activating agent and reacting the so activated porous particulate material with one or more substances which exhibit after being linked as ligand on the porous particulate material, an affinity to the blood coagulation factor to be covered, so as to form a porous matrix having a specific surface area of at least 1.5 m$^2$ per milliliter of the porous particulate material with respect to pores having diameters of at least 0.1 μm.

19 Claims, 3 Drawing Sheets

Fig. 3

SEPARATION MATERIAL DERIVED FROM GLUCOMANNAN FOR BLOOD COAGULATION FACTOR, PREPARATION AND USE THEREOF

FIELD OF THE INVENTION

The present invention relates to a separation material for separating and recovering a blood coagulation factor comprising a porous matrix having one or more ligands introduced therein and preparation and use thereof. More particularly, it relates to a separation material for separating and recovering a blood coagulation factor, especially for collecting blood coagulation factor VIII efficiently from plasma or samples containing such coagulation factor and to a method of preparation thereof as well as to a process for recovering a blood coagulation factor using the separation material.

BACKGROUND OF THE INVENTION

In the blood of humans and animals, various substances participating in the coagulation of blood (blood coagulation factors) are contained. Various disorders or diseases induced from the shortage or lack of blood coagulation factors have been known. In particular, hemophilia A, due to the lack of blood coagulation factor VIII, occupies almost 80% of the whole of such diseases. There has hitherto been proposed no effective therapy for a radical cure of hemophilia A and, up to date, a therapeutic measure of replenishing the patient with blood coagulation factor VIII on requirement has currently been employed.

Blood coagulation factor VIII consists of a protein having a molecular weight of about 260,000, which is contained in the normal blood plasma only in an amount of about 0.1 $\mu$g/ml. Blood coagulation factor VIII is present in blood plasma under formation of a complex with another blood coagulation factor, namely, von Willebrand factor (abbreviated hereinafter as vWf) composed of proteins having molecular weights of 500,000-20,000,000. In the context of this application, by the word "blood coagulation factor" is meant to include such a complex. In the therapy of hemophilia A, no sufficient replenishment of blood coagulation factor VIII can be achieved by transfusion of an intact whole blood or plasma as such to the patient, since the concentration of blood coagulation factor VIII in the plasma is quite low. It has therefore been a wide spread practice to employ an intravenous injection of a concentrated preparation of blood coagulation factor VIII for such a patient.

It has been practiced to carry out concentration of blood coagulation factor VIII by forming first a cryoprecipitate from blood plasma, separating it and then thawing it to obtain a concentrate, or by employing purification by liquid chromatography and so on. However, the yield of recovery of blood coagulation factor VIII in these prior techniques has been able to reach to a figure of only about a little lower than 10%, based on the weight of the plasma, and even by the technique using a liquid chromatography, to a value of about 20%.

In the technique employing liquid chromatography, separation materials have been employed, in which ligands, such as, substances having affinity to blood coagulation factor VIII or to vWf, for example, substances having aminoalkyl groups (Japanese Patent Kokai Nos. 136518/1985 and 157000/1989), monoclonal antibodies (Japanese Patent Kokai Nos. 13099/1989 and 221396/1989), collagens (Japanese Patent Kokai No. 198632/1988 and so on) and so on are caused to link onto the substrate.

For a separation material for use for recovering blood coagulation factor VIII in a liquid chromatography, the following properties are required:
1) It should not cause any non-specific adsorption of plasma proteins.
2) It should have a pore diameter capable of permeating a complex of blood coagulation factor VIII with vWf and a sufficiently wide internal surface area for making avail of a large adsorption capacity.
3) The substrate to be combined with the ligand should have high stabilities not only in physical but also in chemical properties.

In the conventional techniques mentioned above, separation materials prepared from natural high molecular weight substances, such as, agarose, dextran, cellulose and so on are employed. These separation materials are superior in so far as they employ substrates consisting of natural substances and non-specific adsorption will scarcely occur. For these prior art separation material no quantitative assay as to the properties mentioned in the above 2) has been made, so that it might have hitherto been probable that separation material having lower adsorption capacity are employed with poor recovery yield of blood coagulation factors.

SUMMARY OF THE INVENTION

An object of the present invention is to provide a separation material for separating and recovering a blood coagulation factor which enables the reaching of a high recovery yield of the blood coagulation factor with superior efficiency.

Another object of the present invention is to propose a process for preparing such a separation material in a simple manner.

A further object of the present invention is to provide a process for recovering a blood coagulation factor using the separation material.

Thus, the present invention relates to a separation material for separating and recovering a blood coagulation factor, to a process for preparing it and to the use of the separation material for recovering a blood coagulation factor as given below:

(1) A separation material for separating and recovering a blood coagulation factor, comprises a porous matrix having linked thereon one or more ligands each consisting of a radical exhibiting an affinity to the blood coagulation factor to be recovered, said porous matrix having a specific surface area of at least 1.5 m² per milliliter of separation material with respect to pores having diameters of at least 0.1 $\mu$m and said porous matrix being derived from a porous particulate material having an exclusion limit molecular weight of at least $1.5 \times 10^6$ as determined with polyethylene glycol.

(2) A process for preparing the separation material for separating and recovering a blood coagulation factor, comprising the steps of
subjecting a porous particualte material having an exclusion limit molecular weight of at least $1.5 \times 10^6$ to an activation by 1,1'-carbonyldiimidazolating, tresylating, carbodiimidizing, thiopropylating, epoxidizing, bromocyanizing or formylating by using a corresponding activating agent and reacting the so activated porous particulate material with one or more substances which exhibit, after being linked as ligand on the porous particulate material, an affinity to the blood coagulation factor to be recovered, so as to form a porous matrix having a specific surface area of at least 1.5 m² per milliliter of the particulate material with respect to pores having diameters of at least 0.1 μm.

(3) A process for recovering a blood coagulation factor from a blood coagulation factor-containing raw material using a separation material which comprises a porous matrix having linked thereon one or more ligands each consisting of a radical exhibiting an affinity to the blood coagulation factor to be recovered, said matrix having a specific surface area of at least 1.5 m² per milliliter of the separation material with respect to pores having diameters of at least 0.1 μm and said matrix being derived from a porous particulate material having an exclusion limit molecular weight of at least $1.5 \times 10^6$ as determined with polyethylene glycol, said process comprizing the steps of bringing the raw material into contact with the separation material by the use of an adsorption buffer solution and subjecting the resulting separation material containing the blood coagulation factor adsorbed thereon to elution by contacting it with an eluent buffer solution to collect the blood coagulation factor.

DETAILED DESCRIPTION OF THE INVENTION

The blood coagulation factors which can be recovered by the separation material according to the present invention include, for example, blood coagulation factor VIII, a complex of blood coagulation factor VIII with von Willebrand factor and so on.

For the porous particulate material to be employed for the separation material according to the present invention, there is no special limitation and every porous particulate material can be employed, so long as it has internal pores and channels permitting penetration of the blood coagulation factor to be recovered therethrough and excludes the occurrence of non-specific adsorption of other substances, such as plasma proteins and so on contained in the liquid to be subjected to recovery of blood coagulation factor, and is stable in its chemical and physical natures and yet permits ligands to link thereto by a certain measure, such as activation thereof, as described afterwards.

Examples of such porous material include polysaccharides, such as, glucomannan, pullulan, agarose, starch, cellulose and dextran, organic synthetic polymeric substances, such as, polyvinyl alcohol, polystyrene, ethylene-maleic anhydride copolymer, polyacrylamide and polymethyl methacrylate, inorganic polymeric substances, such as, glass, silica and alumina, as well as composites thereof. In general, these porous materials are present in the form of particles, which may be cross-linked products obtained using an adequate cross linking agent. From the point of view of strength, cross-linked products are preferred. It is also possible to employ commercial packing materials for chromatography.

Among them, cross-linked glucomannan spherical beads formed from glucomannan and exhibiting scarce non-specific adsorption of plasma proteins and the like, and having stable chemical and physical properties, high compressive strength and permit a high velocity liquid flow therethrough are especially preferable. The cross-linked glucomannan spherical beads are hydrophilic gel particles in which glucomannan composed mainly of D-glucose and D-mannose has been cross-linked using a cross linking agent. As the glucomannan raw product, such products as those having molecular weights in the range from $9 \times 10^5$ to $2.4 \times 10^6$, preferably in the range from $1 \times 10^6$ to $1.3 \times 10^6$ are desirable. As a commercially available product, konjakmannan may preferably be employed, though other products may of course be used. For the exclusion limit molecular weight of the cross-liked glucomannan spherical beads, there may be chosen adequate ranges in accordance with each specific purpose.

For the porous matrix of the separation material according to the present invention, those which have exclusion limit molecular weights of at least $1.5 \times 10^6$, preferably in the range of $2 \times 10^6 - 1 \times 10^7$, and even more preferably in the range of $2 \times 10^6 - 5 \times 10^6$, before combination with the ligand, determined using a series of polyethylene glycol standards, and having a specific surface area (namely, "pore inner surface area"), with respect to pores having diameters of at least 0.1 μm, of 1.5 m²/ml of separation material after the combination with the ligand.

The exclusion limit molecular weight of the porous particulate material is determined in such a manner, that aqueous solutions of polyethylene glycol products, each having a known molecular weight, are passed through a column filled with the porous particulate material and each eluted amount of the polyethylene glycol determined using, for example, a differential refractometer or the like, is plotted on a graph against the molecular weight thereof and the molecular weight value at the break of the curve is assumed to be the exclusion limit molecular weight of the porous particulate material.

The porous particulate material is then subjected to a treatment for linking the ligand thereto.

Thus, separation material for recovering a blood coagulation factor according to the present invention contains one or more ligands, each having an affinity to the blood coagulation factor to be recovered, and has a specific surface area with respect to pores having diameters of at least 0.1 μm of 1.5 m²/ml of separation material, preferably at least 2 m²/ml of separation material, and even more preferably at least 3 m²/ml of separation material.

The specific surface area is determined in such a manner that the pore size distribution of a porous separation material is measured by mercury compression technique after drying the separation material under vacuum and, from the thus obtained pore size distribution, the specific surface area per g of the dried separation material in terms of m²/g is calculated and, parallel thereto, a wet volume per dry weight (volume upon immersion in water) in terms of ml/g is determined, whereupon the specific surface area per wet volume is calculated from these two values.

For the ligand to be combined with the separation material according to the present invention, there is no special limitation and every material can be employed so long as they exhibit specific interaction (affinty) with the blood coagulation factor to be recovered. Thus, for example, collagens, monoclonal antibodies and substances having a group expressed by the general formula (I) given below may be employed:

in which $R^1$ and $R^2$ each represent a hydrogen atom or a lower alkyl group and may be identical with or different from each other, l is a number of 0 or 1, m is an integer of 3-8, n equals to 0 or 1 and p is an integer of 0-5.

They may be used solely or in combination of two or more of them.

For the group represented by the general formula (I), in particular, the groups represented by the following formulae (II) and (III) may be enumerated in which $R^1$ and $R^2$ have the same meaning as in the general formula (I), l denotes a number of 0 or 1, m represents an integer of 3-8 and p is an integer of 2-5.

Concrete examples of the group represented by the general formula (II) include 4-aminobutyl [—CH$_2$(CH$_2$)$_3$NH$_2$], 6-aminohexyl [—CH$_2$(CH$_2$)$_5$NH$_2$], 4-aminobutylamino [—NH(CH$_2$)$_4$NH$_2$], 6-aminohexylamino [—NH(CH$_2$)$_6$NH$_2$] and so on.

Concrete examples of the group represented by the general formula (III) include 4-aminobutylcarbamylbutyl [—CH$_2$(CH$_2$)$_3$C(=O)NH(CH$_2$)$_4$NH$_2$], 3-aminopropylcarbamylbutyl [—CH$_2$(CH$_2$)$_3$C(=O)NH(CH$_2$)$_3$NH$_2$], dimethylaminobutylcarbamylbutyl [—CH$_2$(CH$_2$)$_3$C(=O)NH(CH$_2$)$_4$N(CH$_3$)$_2$], dimethylaminopropylcarbamylbutyl [—CH$_2$(CH$_2$)$_3$C(=O)NH(CH$_2$)$_3$N(CH$_3$)$_2$], dimethylaminopropylcarbamylpentyl [—CH$_2$(CH$_2$)$_4$C(=O)NH(CH$_2$)$_3$N(CH$_3$)$_2$], 4-aminobutylcarbamylbutylamino [—NH(CH$_2$)$_4$C(=O)NH(CH$_2$)$_4$NH$_2$], 3-aminopropylcarbamylbutylamino [—NH(CH$_2$)$_4$C(=O)NH(CH$_2$)$_3$NH$_2$], dimethylaminobutylcarbamylbutylamino [—NH(CH$_2$)$_4$C(=O)NH(CH$_2$)$_4$—N(CH$_3$)$_2$], dimethylaminopropylcarbamylbutylamino [—NH(CH$_2$)$_4$—C(=O)NH(CH$_2$)$_3$N(CH$_3$)$_2$], dimethylaminopropylcarbamylpentylamino [—NH(CH$_2$)$_5$C(=O)NH(CH$_2$)$_3$N(CH$_3$)$_2$] and so on.

For the collagen, there may be employed preferably a limited decomposition product of a collagen IV by treating it with an enzyme, such as, pepsin or the like, collagen III and so on.

The ligand may be combined directly to the porous matrix or through an adequate spacer.

The ligand can be introduced into the separation material according to the present invention after specific portions have been activated by 1,1'-carbonyldiimidazolating, tresylating, carbodiimidizing, thiopropylating, epoxidizing, bromocyanizing or formylating using corresponding activating agent.

For the activating agent, there may be employed, for example, 1,1'-carbonyldiimidazole, tresyl chloride (namely, 2,2,2-trifluoroethane sulfonyl chloride), 1-ethyl-3-(3-dimethylaminopropyl)carbodiimide hydrochloride, 1,4-butanediol glycidyl ether, glutaraldehyde, hexamethylene diisocyanate, cyanogen bromide, bisoxirane, 1,4-bis(2,3-epoxypropoxy) butane and so on.

Now, description will be directed to the cross-linked glucomannan spherical beads to be employed as the porous particulate material for the separation material according to the present invention.

Cross-linked glucomannan spherical beads before being combined with the ligand can be obtained by subjecting spherical glucomannan to a cross linking reaction. Below, one concrete example of the production of cross-linked glucomannan spherical beads is explained.

A commercially available glucomannan product is dissolved, after it has been purified using alcohol or the like, in a solvent such as formamide or dimethylformamide. Using this glucomannan solution, an ester of glucomannan is prepared using a catalyst, for example pyridine, by adding to the solution an acid, such as, acetic acid, acetic anhydride, propionic acid, butylic acid, nitric acid or so on. The obtained glucomannan ester is dissolved in a solvent together with a porosifying agent, namely, an agent for producing porous structure. For the solvent, those which have a lower boiling point as compared with the aqueous medium explained below and which do not or only scarcely dissolve in the aqueous medium may be employed. Concrete examples of such a solvent include organic solvents based on a chlorinated hydrocarbon, such as, dichloromethane, chloroform, carbon tetrachloride and trichloroethylene, which may be employed solely or in mixture. As the glucomannan ester, there may be employed those which have viscosity values of 8-20 cP, preferably 9-12 cP, determined at 30° C. in a chloroform solution at a concentration of about 0.3% by weight. The concentration of the glucomannan ester on preparing its solution may be 0.5-10 g, preferably 0.5-2 g, per 100 ml of the solvent. The porosifying agent is employed for producing a porous structure in the spherical beads of glucomannan ester by being included in the liquid droplet of the glucomannan ester solution. Most of the porosifying agent will be removed upon the saponification of the particles resulting from the glucomannan ester droplet, thus leaving micropores and channels inside the gelled particle. Concrete examples of the porosifying agent include decalin (decahydronaphthalene), methyl n-caprinate, tetrahydronaphthalene, ethylbenzene, diethybenzene, methyl dodecanoate, toluene, hexyl alcohol, heptyl alcohol and octyl alcohol, all of which may have higher boiling points than that of the above mentioned organic solvent and do not dissolve the glucomannan ester. The concentration of the porosifying agent may be in the range from 1 to 5 ml, preferably in the range from 2 to 4 ml per g of the glucomannan ester. The thus obtained glucomannan ester solution as explained above is suspended in an aqueous medium, in order to cause formation of liquid droplets of the glucomannan solution. For the aqueous medium, water or an aqueous solution having added therein a hydrophilic protective colloid, such as, polyvinyl alcohol, partially saponified polyvinyl alcohol, carboxymethyl cellulose, ethyl cellulose, methyl cellulose, soluble starch, gelatin or so on, may be employed. Hydrophilic protective colloids may be employed in an aqueous solution at a concentration in the range of from 0.1 to 10% by weight, preferably from 1 to 5% by weight. The amount of the aqueous medium employed should be at least 2-fold, preferably 10–50 times the volume of glucomannan ester solution.

For preparing the suspension of glucomannan ester solution droplets in the aqueous medium, it is possible to carry out in such a manner, that the glucomannan ester solution is introduced into the aqueous medium all at once and the mixture is dispersed under agitation to form a liquid droplet suspension, or in such a manner, that the aqueous medium is held under agitation and the glucomannan ester solution is introduced therein all at once or dripped thereinto.

The glucomannan ester solution will suspend in the aqueous medium in a finely dispersed form, since it is insoluble in water. Then, granulation from the droplets of the glucomannan ester solution occurs by vaporization of the organic solvent. In this manner, spherical beads of the glucomannan ester are formed, from which the organic solvent has substantially been removed.

The temperature for formation of spherical beads of the glucomannan ester in the aqueous medium is selected to be at a point lower than the boiling point of the organic solvent and higher than the freezing point of the aqueous medium. Here, it is preferably to choose the temperature during the course of formation of the glucomannan ester beads, while evaporating off the organic solvent, at a point which is 1°–5° C. lower than the boiling point of the organic solvent, in order to facilitate vaporization of the organic solvent and to preserve the spherical shape of the liquid droplet.

The contemplated spherical beads will be obtained by agitating the aqueous medium, wherein a desired particle size can be realized by adjusting the intensity of the agitation. It is enough to choose the agitation condition in the process according to the present invention, so as to form beads having a particle size adapted for use as the separator medium, namely, a particle size in a range from 1 to 500 μm.

Thereafter, the so formed spherical beads of glucomannan ester are subjected to saponification. Here, it is necessary to employ a saponification bath capable of effecting saponification, while maintaining the original spherical form of the beads without deteriorating their spherical form. Examples of such a saponification bath include methanolic solutions of sodium hydroxide or potassium hydroxide, solutions of sodium hydroxide or potassium hydroxide in an aqueous solution of salts, such as, sodium sulfate and so on.

By bringing the glucomannan ester beads into contact with the saponification bath, the beads will be saponified, while most of the porosifying agent included in the beads is removed therefrom leaving fine pores therein.

An almost 100% saponification of the glucomannan ester beads will be attained by employing a reaction condition of a temperature of 10°–50° C. and a reaction time of 0.5–24 hours.

The resulting saponified spherical beads of glucomannan is subjected to cross linking. As the cross linking agent, there may be employed, for example, bifunctional compounds, such as, epichlorohydrin, diepoxybutane, tolylene diisocyanate, hexamethylene diisocyanate and so on. The cross linking agent is employed in a form of a solution dissolved in an organic medium.

As the organic solvent for the cross linking agent, there may be employed, for example, kerosene, liquid paraffin and mixtures of them (in a volume ratio of, for example, 7:3), to which a surfactant (a nonionic surfactant, such as, an aliphatic ester of sorbitan) is added in an amount of 1–2% by weight, or a mixture of acetone and dimethylsulfoxide (in a volume ratio of, for example, 6:4), or further, a mixture of acetone with dimethylformamide (in a volume ratio of, for example, 2:3) etc. The concentration of the cross linking agent may preferably in the range of from 0.01 to 15 moles per liter of the organic solvent.

The spherical beads of saponified glucomannan are then cross-linked by introducing 1–5 parts by weight of the saponified glucomannan spherical beads into 100 parts by volume of the cross linking agent solution and holding the mixture under agitation for 24–36 hours at a temperature of from room temperature to 70° C. The degree of cross linking can be adjusted by selecting the concentration of the cross linking agent. Cross-linked spherical beads of glucomannan having an exclusion limit molecular weight of at least $1.5 \times 10^6$ will be obtained by filtering off, washing with acetone and then with a neutral detergent, followed by water wash, of the so reacted beads.

The thus obtained cross-linked spherical beads of glucomannan exhibit a high persistency to compression and considerable stabilities in both mechanical and chemical properties. They are almost insusceptible to various organic solvents and salt solutions and show almost no swelling nor contraction. Thus, they do not suffer from alteration of the cell structure, deformation and fusion of beads, even when the ligands are introduced with an organic solvent with simultaneous presence of salts, as described afterwards. Therefore, a separation material according to the present invention having sufficient pore size, specific surface area, ligand concentration and adsorption capacity can be prepared from such beads. Moreover, an autoclave pasteurization of the beads can be employed, since glucomannan beads thus obtained have superior thermal stability.

While a detailed explanation of a practical manner of producing the porous particulate material for use for the preparation of the separation material according to the present invention from glucomannan has been given above, it is also possible to employ other starting material, such as the polysaccharides mentioned previously, for producing porous particulate material having an exclusion limit molecular weight of at least $1.5 \times 10^6$ by similar procedures.

Now, the description is directed to the concrete manner of introducing the ligand into the thus obtained porous particulate material or beads.

The porous particulate material or beads produced as above are first soaked in a medium for effecting the reaction of the beads with an activating agent for pretreatment for the reaction with the ligand, in order to cause them to swell sufficiently by the medium and, at the same time, to exclude any air bubble entrained therein. For the reaction medium, those which will adapt to the subsequent pretreatment reaction of the porous beads with the activating agent are used. As a suitable medium, there may be employed dimethylformamide, a mixed liquid composed of acetone andpyridine, an aqueous solution of sodium hydrogen borate withsodium hydroxide and so on.

To the resulting swollen porous beads soaked in the reaction medium, an activating agent is added in an amount sufficient to realize the pretreatment reaction, in order to cause activation of the inner cellular surfaces of the porous beads. The activation is incorporated, in order to cause the ligand molecules to link onto certain sites over the inner surfaces of the porous beads. The activation is carried out practically by, for example, 1,1'-carbonyldiimidazolating, tresylating, carbodiimidizing, epoxidizing, thiopropylating, bromocyanizing or formylating the above mentioned sites inside the cellular matrix of the bead. The amount of the activating agent employed depends on each specific activating agent employed and, in general, ranges from 2 to 200 parts per 100 parts by weight of the dry beads. For the condition of activation, a reaction temperature in the range from 0° to 50° C. and a reaction duration in the range from 5 minutes to 3 hours may be applicable. The followings are exemplifications of the concrete ways for carrying out the activation of the porous beads according to the present invention:

In the 1,1'-carbonyldiimidazolation, the porous beads are reacted with 1,1'-carbonyldiimidazole in a reaction medium of dimethylformamide.

In the tresylation, the porous beads are reacted with tresyl chloride in a reaction medium of a mixed liquid composed of acetone and pyridine.

In the thiopropylation, the porous beads are first reacted with epichlorohydrin, then, with thiosulfuric acid, whereupon the resulting beads are subjected to a reduction with dithiothreitol, followed by disulfidation using 2,2'-dipyridyldisulfide.

In the epoxidation, the porous beads are reacted with a bisoxirane, such as, 1,4-butanediol diglycidyl ether, in a 0.3M aqueous solution of sodium hydroxide containing sodium hydrogen borate.

In the bromocyanidation, the porous beads are reacted with cyanogen bromide in an aqueous solution of sodium hydroxide of a pH of 11-12.

After the activation reaction has been completed, the remaining excess amount of the activating agent is removed by separating the thus activated porous beads from the reaction medium by, for example, filtering them out of the medium and then subjecting them to sufficient washing. While there can be selected for washing the reacted beads various adequate liquids, it is preferable, in the case of employing tresyl chloride as the activating agent and a mixed solvent composed of acetone and pyridine as the reaction medium, to choose a mixed solution composed of acetone and a low concentration aqueous solution of hydrochloric acid as the washing liquid.

The so activated porous beads are then combined with one or more suitable ligands having affinity to the blood coagulation factor to be recovered, by contacting the so activated porous beads with a solution containing such one or more ligands under sufficient mixing to cause intimate contact of the porous beads with the solution. Here, as for the reaction condition, a temperature usually in the range from 0° to 40° C. and a reaction duration usually in the range from 15 minutes to 24 hours may be employed. The solution containing the ligand may be prepared by dissolving each selected ligand or ligands in an adequate buffer solution. Usually, the ligand solution is used preferably in such an amount that the ligand or ligands in the solution will be present at least in a stoichiometric amount for reacting with the activated sites in the beads.

The porous beads now having the selected one or more ligands linked thereto are separated from the reaction medium by being filtered off or in other similar ways and washed sufficiently. The washing liquid can adequately be selected and, for example, an aqueous solution of sodium chloride, an acetate buffer solution containing sodium chloride, a bicarbonate buffer solution containing sodium chloride, pure water and various organic solvents may be chosen therefor.

The unreacted active sites in the porous beads, namely, the vacant activated sites not combined with any ligand, are then blocked with an adequate blocking agent. The blocking can be effected by immersing the porous beads in a solution of an adequate blocking agent at a temperature of 0°–40° C. for a duration in the range from 30 minutes to 24 hours. For the blocking agent, there may be exemplified monoethanolamine, a tris-hydrochloric acid buffer solution containing sodium chloride and so on.

In the case of activating the porous beads with 1,1'-carbonyldiimidazole and the thus activated beads are combined with a ligand having a group expressed by the formula (I) given previously, the resulting separation material has a structure represented by the following general formula in which A represents the porous particulate material and $R^1$, $R^2$, m, n and p have the same meaning as given previously in explaining the general formula (I).

While there is no restriction for the amount of one or more ligands (denoted hereinafter as ligand concentration) linked in the porous beads, it is preferable to choose such a ligand concentration that it suffices the requisite amount of blood coagulation factor(s) to be adsorbed on the separation material.

When cross-linked glucomannan beads have one or more ligands linked thereto, as described above, the resulting separation material will have nearly the same exclusion limit molecular weight as that of the intact starting cross-linked glucomannan beads. The separation material prepared by introducing one or more ligands into cross-linked spherical glucamannan beads is excellent in its persistency against compression, so that it permits operation at high flow velocity, resulting in an increase in the hourly treatment output.

There is no limitation in the manner of employment of the separation material for recovering a blood separation factor according to the present invention. The separation material according to the present invention is directed for use for recovery of a blood coagulation factor, especially, blood coagulation factor VIII and complex of the blood coagulation factor VIII with vWf. The separation material according to the present invention may be employed for recovering a blood coagulation factor from various substances (hereinafter denoted as raw substances), for example, blood plasma, cryoprecipitates, Cohn fractions, blood coagulation factor-containing material resulting from culture of cells secreting blood coagulation factors and so on.

The separation of a blood coagulation factor from the raw substances using the separation material according to the present invention may be realized by known methods, such as, by using an elution column (column method) and step-wise equilibrium on batches (batch method), in which the raw substances and the separation material according to the present invention are brought into contact with each other within an adequate adsorption buffer solution, so as to cause the contemplated blood coagulation factor to adsorb on the separation material. The resulting separation material on which the blood coagulation factor has been adsorbed is then subjected to desorption by immersing the separation material in an adequate desorption buffer solution to recover the desorbed blood coagulation factor.

As the adsorption buffer solution to be employed in the column method, there may be employed those which develop a pH within the range from 4.5 to 9.5, preferably from 5.5 to 8.8. As the typical adsorption buffer solution, there may be enumerated, for example, bis-tris-hydrochloric acid (pH range: 5.5–7.3), triethanolamine-hydrochloric acid (pH range: 7.3–7.7), diethanolamine-hydrochloric acid (pH range: 8.4–8.8) and buffer solutions which are obtained by adding to the above-mentioned buffer solutions about 1 mM of calcium chloride and about 100 mM of sodium chloride. For the typical desorption buffer solution, there may be employed those buffer solutions in which the buffer solutions mentioned above for the typical adsorption buffer solution are modified by adding about 0.5–3M of sodium chloride and about 500 mM of calcium chloride.

For practicing the separation treatment, the buffer solution for the adsorption should preferably be selected among the above-mentioned buffer solutions such as one that develops a pH value as near as possible to that of the raw substance to be treated.

For effecting practical adsorption, usually a linear flow velocity (LV) of 5–500 cm/hr, preferably 50–300 cm/hr of the adsorption buffer solution containing the raw substance through the column filled with the separation material according to the present invention may be employed. For desorption, the desorption buffer solution may be passed through the column after the adsorption step at a linear flow velocity usually of 5–500 cm/hr, preferably from 50 to 300 cm/hr.

In a batch method, the separation material according to the present invention and the raw substance containing the blood coagulation factor are brought together at room temperature and the mixture should preferably be shaken for a period of at least 10 minutes under enough shaking to reach a sufficient mixing of the seapration material with the raw substance. Also in the batch method, the same buffer solutions as used in the column method can be employed.

Since the separation material for a blood coagulation factor according to the present invention has been derived from a porous particulate material having an exclusion limit molecular weight of at least $1.5 \times 10^6$, a blood coagulation factor or vWf complex can penetrate therethrough smoothly. Due to the large specific surface area of at least 1.5 $m^2$/ml of the separation material, the raw substance can be entrapped by the ligand radicals linked on the inner surface quite efficiently. The greatly increased capacity of the separation material according to the present invention for adsorbing a blood coagulation factor or vWf complex in the raw substance is believed to be due to the above reasons.

Cross linking of beads of glucomannan may cause the specific surface area and the inner pore size to tend to increase, and nevertheless, the resistance or persistency against compression becomes improved. This is believed to be due to a possible increase in the cell wall thickness by the cross linking. It is assumed that the increase in the pore size by the cross linking gives birth to the smooth passage of the blood coagulation factors, especially blood coagulation factor VIII and the complex of blood coagulation factor VIII with von Willebrand factor.

As described above, a separation material for a blood coagulation factor can be obtained according to the present invention, which permits the separation and recovery of a blood coagulation factor, especially blood coagulation factor VIII in a high yield efficiently. In particular, when porous beads of cross-linked glucomannan are employed for the starting porous particulate material, a separation material capable of separating and recovering a blood coagulation factor more efficiently can be obtained, since they exhibit high persistency against compression and thus permit employment of high flow velocity for the column method.

In addition, the present invention proposes an easy method of preparation of the separation material for a blood coagulation factor exhibiting superior properties as explained above.

PREFERRED EMBODIMENT

Below, the present invention is further described concretely by way of Examples. By "Unit" as used herein for expressing the concentration of blood coagulation factor VIII, is meant "unit of coagulant activity of blood coagulation factor VIII".

PRODUCTION EXAMPLES FOR CROSS-LINKED GLUCOMANNAN BEADS

Porous spherical beads of cross-linked glucomannan for use as the matrix or substrate of the separation material according to the present invention are produced by the following procedures:

I. Production of Spherical Bead Product $A_1$ of Cross-linked Glucomannan 60 g of konjakmannan powder were dissolved in 6 liters of tap water at a temperature of about 80° C. with agitation. The resulting solution was dropped slowly into 6 liters of ethanol so as to form precipitate of glucomannan. The precipitate was separated by filtration and dried in air. The air-dried precipitate was then dried under vacuum to obtain purified glucomannan product (hereinafter GM is used sometime for glucomannan).

30 g of the purified glucomannan product were introduced in 1 liter of formamide and allowed to stand for 7 hours at 55° C. to cause swelling of the product. Then, 300 ml of pyridine was added thereto. After 2 hours, 300 ml of acetic anhydride were added thereto and the reaction was conducted at 55° C. for 4 days to esterify the glucomannan product. This reaction mixture was poured into 7 liters of water with agitation. The precipitate formed was separated by filtration, washed with water, dried in air and then dried under vacuum. The so obtained raw acetate product was dissolved in 10 liters of acetone. After removal of the insoluble matter, the solution was introduced into about 20 liters of water with agitation. The precipitate formed was separated by filtration and dried in air. Then, it was dried under vacuum to obtain glucomannan acetate product A. A chloroform solution of this acetate product A of a concentration of 0.29 wt. % exhibited a viscosity of 10 cP at 30° C.

10 g of the acetate product A were dissolved together with 35 milliliters of methyl n-caprinate as the porosifying agent into 560 milliliters of chloroform. This solution was dropped into 5 liters of 1 wt. % aqueous solution of a 90%-saponified polyvinyl alcohol at 55° C. with agitation at an agitation rate of 600 rpm. and the agitation was continued. After 24 hours, the solution was allowed to stand for gradual cooling and the thus formed spherical particles were then separated by filtration and washed with water.

The spherical particles were then introduced into a mixed solution of 225 milliliters of methanol and 25 milliliters of 10N aq. NaOH and the particles were subjected to saponification for 2 hours with agitation.

The resulting saponified spherical particles were separated by filtration, added to a mixture composed of 200 milliliters of acetone, 300 milliliters of dimethylformamide and 70 milliliters of epichlorohydrin and subjected to cross linking for 24 hours at 60° C. The particles were then collected, washed with water and subjected to extraction with acetone to obtain spherical beads $A_1$ of cross-linked glucomannan (hereinafter abbreviated as $GM-A_1$).

II. Production of Cross-linked Glucomannan Beads $A_2$ 10 g of the above acetate product A were dissolved together with 28 milliliters of decalin as the porosifying agent in 740 milliliters chloroform. This solution was dropped into 5 liters of an 1 wt. % aqueous solution of a 90%-saponified polyvinyl alcohol at 55° C., while agitating at an agitation rate of 600 rpm. and the agitation was continued. The vessel for particulation, namely particle formation, had baffle plates provided on its inner walls. Thereafter, the same procedures as in the production of $GM-A_1$ were followed to obtain a cross-linked glucomannan beads product $A_2$ (hereinafter abbreviated as $GM-A_2$).

III. Production of Cross-linked Glucomannan Beads $A_3$ 10 g of the above acetate product A were dissolved together with 30 milliliters of decalin as the porosifying agent in 740 milliliters chloroform. This solution was dropped into 5 liters of 1 wt. % aqueous solution of a 90%-saponified polyvinyl alcohol at 55° C., while agitating at an agitation rate of 600 rpm. and the agitation was continued. The vessel for particulation had baffle plates provided on its inner walls. Thereafter, the same procedures as in the production of $GM-A_1$ were followed to obtain a cross-linked glucomannan beads product $A_3$ (hereinafter abbreviated as $GM-A_3$).

IV. Production of Cross-linked Glucomannan Beads $B_1$

The procedures for the production of $GM-A_1$ were followed except that the porosifying agent methyl n-caprinate was replaced by decalin and the agitation rate was changed to 500 rpm., whereby a cross-linked glucomannan beads $B_1$ (hereinafter abbreviated as $GM-B_1$) was obtained.

V. Production of Cross-linked Glucomannan Beads $B_2$ 15 g of the purified glucomannan product obtained in the course of production of $GM-A_1$ were introduced into 150 milliliters of 1:1 mixture (by volume) of formamide and pyridine and the mixture was allowed to stand for 12 hours at room temperature to cause swelling of the product. The thus swollen glucomannan product separated from the supernatant liquid was introduced into a kneader together with 85 milliliters of acetic anhydride to conduct esterification for 4 days at 50° C. The reaction mixture was processed in the same procedures as in the production of $GM-A_1$ to obtain glucomannan acetate product B. A 0.29 wt. % solution of this acetate product B exhibited a viscosity of 2.5 cP at 30° C.

Thereafter, the same procedures as in the production of $GM-A_1$ were followed to obtain a cross-linked glucomannan beads product $B_2$ (hereinafter abbreviated as $GM-B_2$).

VI. Material Properties of Cross-linked Glucomannan Beads

Exclusion limit molecular weight was determined for the beads products $GM-A_1$ to $GM-A_3$, $GM-B_1$ and $GM-B_2$ using a series of standard polyethylene glycol products.

The results are given in Table 1.

Further, the relationship between the flow velocity and the pressure drop on passing water through a stainless column having an inner diameter of 6 mm and a length of 100 mm and charged with each of the above-mentioned beads products was detected using a high pressure pump and observing the indications of pressure gauges. The results are also given in Table 1

TABLE 1

| GM Product | Bead Diameter (μm) | Exclusion Limit Mol. Weight | Max. permissible Flow Rate (ml/min.) |
|---|---|---|---|
| $GM-A_1$ | 32-125 | $1.7 \times 10^6$ | >10 |
| $GM-A_2$ | 20-44 | $3 \times 10^6$ | >10 |
| $GM-A_3$ | 20-44 | $5 \times 10^6$ | >10 |
| $GM-B_1$ | 32-94 | $1 \times 10^6$ | >10 |
| $GM-B_2$ | 32-76 | $>1 \times 10^7$ | >10 |

From the data given in Table 1, it is seen that all the cross-linked glucomannan spherical beads products had a linear relationship between the flow rate and the pressure drop, even under the condition of high flow velocity, showing thereby a high resistance or persistency against compression.

VII. Preparation of Ligand-linked Separation Material

1) Cross-linked Glucomannan Beads

Ligand of aminobutylamino radical, aminohexylamino radical or aminobutylcarbamylbutylamino radical was introduced into each of the beads products $GM-A_1$ to $GM-A_3$ and $GM-B_1$ and $GM-B_2$ obtained as above, in the following manner:

1-a) Introduction of Aminohexylamino Radical

Each of the cross-linked glucomannan beads products $GM-A_1$ to $GM-A_3$ and $GM-B_1$ and $GM-B_2$ was washed with water and then with acetone while filtering under a negative pressure, before they were dried under vacuum. A predetermined amount of the dried beads of cross-linked glucomannan was introduced into a predetermined amount of dimethylformamide (occasionally abbreviated hereinafter as DMF) and thereto was added a predetermined amount of 1,1'-carbonyldiimidazole (sometimes abbreviated hereinafter as CDI) and the mixture was shaken for a predetermined period of time. The resulting CDI-activated beads were separated by negative pressure filtration and were washed with DMF.

A predetermined amount of the so washed CDI-activated beads was introduced into a predetermined amount of DMF and thereto was added a predetermined amount of 1,6-diaminohexane (occasionally abbreviated as DAH) and the mixture was shaken for a predetermined period of time. The resulting beads having introduced therein aminohexylamino radical were separated by sucking filtration and were washed with DMF and then with water to obtain each of separation material products $A_1$ to $A_3$, $B_1$ and $B_4$. These bead products linked with an aminohexylamino radical were stored in a 20 vol. % aq. ethanol solution. The above procedures were carried out at room temperature. The conditions for introducing the ligand radical are given in Table 2.

1-b) Introduction of Aminobutylamino Radical

The same procedures as in the introduction of the aminohexylamino radical were followed except that 1,4-diaminobutane (occasionally abbreviated hereinafter as DAB) was employed instead of 1,6-diaminohexane, whereby a separation material product $B_2$ was obtained. The conditions for introducing the ligand are given in Table 2.

1-c) Introduction of Aminobutylcarbamylbutylamino Radical

A predetermined amount of 5-aminovaleric acid was dissolved in a mixture of a predetermined amount of DMF with a small amount of aqueous NaOH solution containing an equivalent amount of NaOH. To this solution was added the washed CDI-activated beads obtained in a similar manner as in the introduction of the aminohexylamino radical described above, whereupon the mixture was shaken for 17 hours to cause a reaction of 5-aminovaleric acid with the CDI-activated sites in the beads. The resulting beads were separated from the medium by filtration under a negative pressure then washed with water, 0.05N hydrochloric acid, water and finally with DMF, in this sequence.

The washed beads were introduced into a predetermined amount of DMF and thereto was added a predetermined amount of N-hydroxysuccinimide and 1-ethyl-3-(3-dimethylaminopropyl) carbodiimide hydrochloride, whereupon the mixture was shaken for 26 hours. The thus obtained carbodiimide-activated beads were separated from the reaction mixture by negative pressure filtration and washed with DMF.

The thus washed beads were introduced into a predetermined amount of an aqueous solution of 1,4-diaminobutane containing 0.1M $NaHCO_3$ and 0.5M NaCl and the mixture was shaken for 2.5 hours. The resulting beads having linked aminobutylcarbamylbutylamino radicals were separated from the reaction mixture by negative pressure filtration and washed with water to obtain a separation material product $B_3$.

The so obtained beads having linked aminobutylcarbamylbutylamino radicals were stored in a 20 vol. % aq. ethanol solution. The above procedures were carried out at room temperature. The conditions for introducing the ligand radical are given in Table 2.

2) Commercial Porous Beads

Aminohexylamino radicals were introduced into the four commercial bead products, i.e., Sephacryl S-1000 (Trademark; a product of Pharmacia; beads of cross-linked allyldextran obtained using a cross linking agent N,N'-methylene-bis-acrylamide; occasionally abbreviated hereinafter as S-1000), Sepharose CL-4B (Trademark; a product of Pharmacia; beads of agarose; occasionally abbreviated hereinafter as CL-4B), Sepharose CL-2B (Trademark; a product of Pharmacia; beads of agarose; occasionally abbreviated hereinafter as CL-2B) and Toyopearl HW-75C (Trademark; a product of Tosoh K. K.; beads of a hydrophilic vinylpolymer; occasionally abbreviated hereinafter as HW-75C).

2-a) Introduction of Aminohexylamino Radicals into Sephacryl S-1000

8 milliliters of wet Sephacryl S-1000 beads taken by a messcylinder were filtered under a negative pressure and washed with DMF to replace the soaking medium. The beads were then introduced into 16 milliliters of DMF and thereto was added CDI in an amount of 500 µM/ml gel and the mixture was shaken for 30 minutes at 25° C. The resulting CDI-activated beads were separated from the medium by negative pressure filtration and then washed with DMF.

The washed CDI-activated beads were introduced into 8 milliliters of DMF containing DAH in an amount of 500 µM/ml gel and the mixture was shaken at 25° C. for 30 minutes. The resulting Sephacryl S-1000 having linked aminohexylamino radicals were collected by negative pressure filtration and washed with DMF and then with water to obtain a separation material product $A_4$. This separation material product $A_4$ was stored in a 20 vol. % aq. ethanol solution. The conditions of the introduction of the ligand are given in Table 2.

2-b) Introduction of Aminohexylamino Radicals into Sepharoses CL-4B and CL-2B

Commercial bead products of Sepharoses CL-4B and CL-2B were subjected to solvent replacement by the normal practice from "as sold" state without drying to DMF-soaked state and were activated with CDI.

The so obtained CDI-activated beads were processed in the same procedures as in the introduction of aminohexylamino radicals into the beads of cross-linked glucomannan, whereby separation material products $B_5$ and $B_6$ were obtained. The conditions for introducing the ligand are given in Table 2.

2-c) Introduction of Aminohexylamino Radicals into Toyopearl HW-75C.

7 milliliters of Toyopearl HW-75C were separated from a fine particle fraction, washed with water and then with acetone while filtering under a negative pressure and then dried under a vacuum. This dried Toyopearl HW-75C was introduced into 14 milliliters of DMF and thereto was added CDI in an amount of 500 µM/ml gel and the mixture was shaken for 30 minutes at 25° C. The resulting CDI-activated beads were separated by filtration under a negative pressure and washed with DMF.

The washed CDI-activated beads were introduced into 7 milliliters of DMF containing DAH in an amount of 500 µM/ml gel and the mixture was shaken for 30 minutes at 25° C. The resulting Toyopearl HW-75C beads having linked aminohexylamino radicals were separated by filtration under a negative pressure and washed with DMF and then with water, whereby a separation material product $B_7$ was obtained. This separation material product $B_7$ was stored in a 20 vol. % aq. ethanol solution. The conditions for introducing the ligand are given in Table 2.

3) Analysis of the Separation Material

The practical procedures for determining the wet apparent volumes of the beads of the separation materials before and after the introduction of ligands into the beads for the products of cross-linked glucomannan and for the commercial products, the ligand concentration and the specific surface area were as follows:

Wet apparent volume of beads: An amount of wet beads were charged into a messcylinder together with an adequate amount of water and the messcylinder contents were allowed to stand for 1 day and the apparent volume of the sedimented layer of beads was observed. The beads in the messcylinder were then dried and the dry weight thereof determined. The quotient of the wet apparent volume of the beads in milliliters measured as above divided by the dry weight thereof in grams is given as "wet apparent volume of beads".

Ligand concentration: A predetermined amount of beads was dried and introduced into a 0.005N aq. HCl and the mixture allowed to stand overnight, whereupon the amount of HCl consumption is determined by titrating it with 0.01N aq. NaOH, from which the ligand concentration is calculated.

Specific surface area (pore inner surface area): Beads of each separation material were vacuum dried and the distribution of sizes of inner pores determined by the mercury compression technique using Poresizer Model 9310 of Micromeritix. The value of specific surface area per unit dry weight ($m^2/g$) obtained from the determination of size distribution of inner pores and the value of wet apparent volume of the beads per dry weight of the beads (ml of beads immersed in water per g dry weight) determined separately were used for calculating the value ($m^2/ml$ separation material) of the specific surface area per unit wet volume of the beads.

The results of the analysis are given in Table 3. Here, the exclusion limit molecular weights for bead products S-1000, CL-4B, CL-2B and HW-75C were determined in the same manner as that for GM-$A_1$.

As may be assessed from the data of Table 3, it is clear that the separation material products $A_1$ to $A_4$ meet the scope of the present invention.

It is seen from the results of Table 3, that the separation material products $B_5$ and $B_6$ show a considerable contraction of the apparent volume of the beads after the introduction of ligands whereas all the other separation material products show no change in the apparent volume of beads regardless of the material of the beads, alteration of ligand species and ligand concentration.

By the way, it was seen by a microscopic inspection, that some deformation and fusion the beads of the products $B_5$ and $B_6$ were detected, whereas there were detected no fusion nor deformation of beads for the other separation material products.

TABLE 2

| Separation Material | Beads Matrix | | CDI-Activat. Cond. | | | Condition of Ligand Introduction | | | |
|---|---|---|---|---|---|---|---|---|---|
| | Matrix | Volume[1] (ml) | CDI (mM) | DMF (ml) | React. Time (hr) | Ligand | Amount (mM) | Solvent | React. Time (hr) |
| $A_1$ | GM-$A_1$ | 6.7 | 2.7 | 13.4 | 0.5 | DAH | 3.4 | DMF 6.7 ml | 0.5 |
| $A_2$ | GM-$A_2$ | 6.7 | 3.1 | 12.5 | 0.5 | DAH | 3.1 | DMF 6.3 ml | 0.5 |
| $A_3$ | GM-$A_3$ | 6.3 | 2.7 | 12.0 | 0.5 | DAH | 3.4 | DMF 6.0 ml | 0.5 |
| $A_4$ | S-1000 | 8.0 | 4.0 | 16.0 | 0.5 | DAH | 4.0 | DMF 8.0 ml | 0.5 |
| $B_1$ | GM-$B_1$ | 7.5 | 3.2 | 15.8 | 0.5 | DAH | 4.0 | DMF 7.9 ml | 0.5 |
| $B_2$ | GM-$B_1$ | 7.5 | 3.2 | 15.8 | 0.5 | DAB | 3.2 | DMF 15.8 ml | 0.5 |
| $B_3$ | GM-$B_1$ | 3.6 | 1.1 | 7.3 | 0.5 | ABA[4] | 1.7 | DMF 2.7 ml aq. NaOH 0.9 ml | 17 |
| $B_4$ | GM-$B_2$ | 7.5 | 3.2 | 15.8 | 0.5 | DAH | 3.2 | DMF 15.8 ml | 0.5 |
| $B_5$ | CL-4B | 11.0 | 2.2 | 11.0 | 0.3 | DAH | 5.5 | DMF 11.0 ml | 0.5 |
| $B_6$ | CL-2B | 12.8 | 2.6 | 12.8 | 0.3 | DAH | 6.4 | DMF 12.8 ml | 0.5 |
| $B_7$ | HW-75C | 7.0 | 3.5 | 14.0 | 0.5 | DAH | 3.5 | DMF 7.0 ml | 0.5 |

| Separation Material | Carbodiimide Activation | | | | DAB Introduction | | |
|---|---|---|---|---|---|---|---|
| | NHS[2] (mM) | EDC[3] (mM) | DMF (ml) | React. Time (hr) | Amt. (mM) | Solvent (ml) | React. Time (hr) |
| $A_1$ | | | | | | | |
| $A_2$ | | | | | | | |
| $A_3$ | | | | | | | |
| $A_4$ | | | | | | | |
| $B_1$ | | | | | | | |
| $B_2$ | | | | | | | |
| $B_3$ | 2.7 | 2.1 | 3.6 | 26.0 | 24.0 | 3.6 | 2.5 |
| $B_4$ | | | | | | | |
| $B_5$ | | | | | | | |
| $B_6$ | | | | | | | |
| $B_7$ | | | | | | | |

Notes:
[1] Wet apparent volume of beads before introduction of ligand.
[2] N-hydroxysuccinimide
[3] 1-ethyl-3-(3-dimethylaminopropyl)carbodiimide hydrochloride
[4] Aminovaleric acid.

TABLE 3

| Separation Material | Beads Matrix | | Beads Wet App. Volume (ml/g) | | Ligand Conc. (μM/ml Sep. Mat.) | Specific Surf. Area $(m^2/ml)^3$ | |
|---|---|---|---|---|---|---|---|
| | Kind | E.L.M.W[1] | Before L.I.[2] | After L.I.[2] | | >0.1[4] μm | over all |
| $A_1$ | GM-$A_1$ | $1.7 \times 10^6$ | 6.7 | 6.7 | 53 | 3.4 | 4.6 |
| $A_2$ | GM-$A_2$ | $3 \times 10^6$ | 6.7 | 6.7 | 71 | 4.3 | 6.2 |
| $A_3$ | GM-$A_3$ | $5 \times 10^6$ | 6.3 | 6.3 | 55 | 2.2 | 3.7 |
| $A_4$ | S-1000 | $1.5 \times 10^6$ | 8.0 | 8.0 | 14 | 1.5 | 12.7 |
| $B_1$ | GM-$B_1$ | $1 \times 10^6$ | 7.5 | 7.5 | 60 | 3.4 | 4.8 |

TABLE 3-continued

| Separation Material | Beads Matrix | | Beads Wet App. Volume (ml/g) | | Ligand Conc. | Specific Surf. Area (m²/ml)³ | |
|---|---|---|---|---|---|---|---|
| | Kind | E.L.M.W¹ | Before L.I.² | After L.I.² | (μM/ml Sep. Mat.) | >0.1⁴ μm | over all |
| $B_2$ | GM-B$_1$ | 1 × 10⁶ | 7.5 | 7.4 | 94 | 3.4 | 4.8 |
| $B_3$ | GM-B$_1$ | 1 × 10⁶ | 3.6 | 3.6 | 65 | 3.4 | 4.8 |
| $B_4$ | GM-B$_2$ | >1 × 10⁷ | 7.5 | 7.4 | 38 | 0.7 | 1.9 |
| $B_5$ | CL-4B | 3 × 10⁵ | 11.0 | 5.6 | 40 | ▲ | ▲ |
| $B_6$ | CL-2B | 5 × 10⁵ | 12.8 | 9.2 | 9 | ▲ | ▲ |
| $B_7$ | HW-75C | 1.2 × 10⁶ | 7.0 | 7.0 | 66 | 3.8 | 16.6 |

Notes
[1] Exlusion limit molecular weight before introduction of ligand
[2] Ligand introduction
[3] m² per milliliter of separation material
[4] With respect to pores of diameters of at least 0.1 μm
▲ Impossible to determine

EXAMPLES 1-4

1) Preparation of Samples (Cryoprecipitates) containing Blood Coagulation Factor VIII To 1 liter of human blood plasma, trypsin inhibitor from soybean, benzamidine and diisopropyl fluorophosphate were added in this sequence over a period of about 15 minutes while maintaining the temperature within the range from 0° to 10° C. so that the concentrations of these additives became 100 mg/l, 1.5 g/l and 1 mM respectively.

Thereto was then added a polyethylene glycol product (molecular weight 4000) in an amount of 1% by weight and the mixture was agitated for 30-40 minutes. Ethanol was dropped thereinto at a temperature of 0°-2° C. over a period of 40-50 minutes gradually until a concentration of 3 vol. % was reached and the mixture was maintained at that temperature for about 1 hour with frequent agitation.

After 1 hour, the mixture was centrifugated at 4° C. The precipitate was dissolved in 40 ml of a 55 mM citrate buffer (pH 7.4). This was subjected to centrifugation again and the supernatant was collected and warmed to 26° C. To this supernatant was added a 2.6M glycine solution (including 0.3M NaCl and 25 mM tris-hydrochloride buffer; pH 6.8) warmed to 26° C., so as to reach a glycine concentration of 2M and the mixture was agitated for 30 minutes.

Then, the mixture was subjected to centrifugation at 26° C. and the supernatant was collected. To this supernatant, sodium chloride was added at a temperature of 20°-23° C. so as to reach a NaCl concentration of 90.6 g/l and the mixture was agitated. This mixture was then subjected to centrifugation at room temperature and the resulting precipitate was dissolved in a 55 mM citrate buffer solution (pH 7.4) to obtain a cryoprecipitate solution.

The quantitative analysis of blood coagualtion factor VIII was carried out using Testteam (Trademark) F VIII (a product of Kabi Vitrum AB, Sweden) by the endpoint method.

The samples containing blood coagulation factor VIII used in the experiment were as given in Table 4.

TABLE 4

| Sample | Conc. of Blood Coag. Fact. VIII |
|---|---|
| Cryoprecipitate Soln. A | 0.90 (Units/ml) |
| Cryoprecipitate Soln. B | 1.25 (Units/ml) |
| Cryoprecipitate Soln. C | 1.39 (Units/ml) |
| Cryoprecipitate Soln. D | 1.81 (Units/ml) |

TABLE 4-continued

| Sample | Conc. of Blood Coag. Fact. VIII |
|---|---|
| Cryoprecipitate Soln. E | 0.649 (Units/ml) |

2) Experiments for Separating Blood Coagulation Factor VIII 2-a) Adsorption Experiments in Batch Method In a 1.5 ml Eppendorf sample vial, a predetermined amount of beads of each separation material was charged and the beads were washed with buffer solution B (20 mM tris-hydrochloride, 500 mM CaCl$_2$, 2M NaCl; pH 7.4) and then with buffer solution A (20 mM tris-hydrochloride, 1 mM CaCl$_2$, 100 mM NaCl; pH 7.4).

To this vial, a predetermined amount of each of the cryoprecipitate solutions was added and the mixture was agitated at room temperature for 1 hour. Then, the mixture was subjected to centrifugation at 10,000 rpm. for 3 minutes. The supernatant was collected and the blood coagulation factor VIII thereof was quantitatively determined in the same manner as that in the preparation of the sample.

With respect to the separation material product $A_1$ and $A_2$, the relationship between the concentration of blood coagulation factor VIII determined as above and the amount of adsorption of blood coagulation factor VIII per milliliter of the separation material was detected. On the other hand, the difference between the concentration of blood coagulation factor VIII in the loaded cryoprecipitate and the concentration of blood coagulation factor VIII in the supernatant after the adsorption was detected and the proportion in % of this difference to the concentration of the blood coagulation factor VIII in the loaded cryoprecipitate is denoted as adsorption rate of blood coagulation factor VIII. The results are summarized in Table 5.

Figure 1:
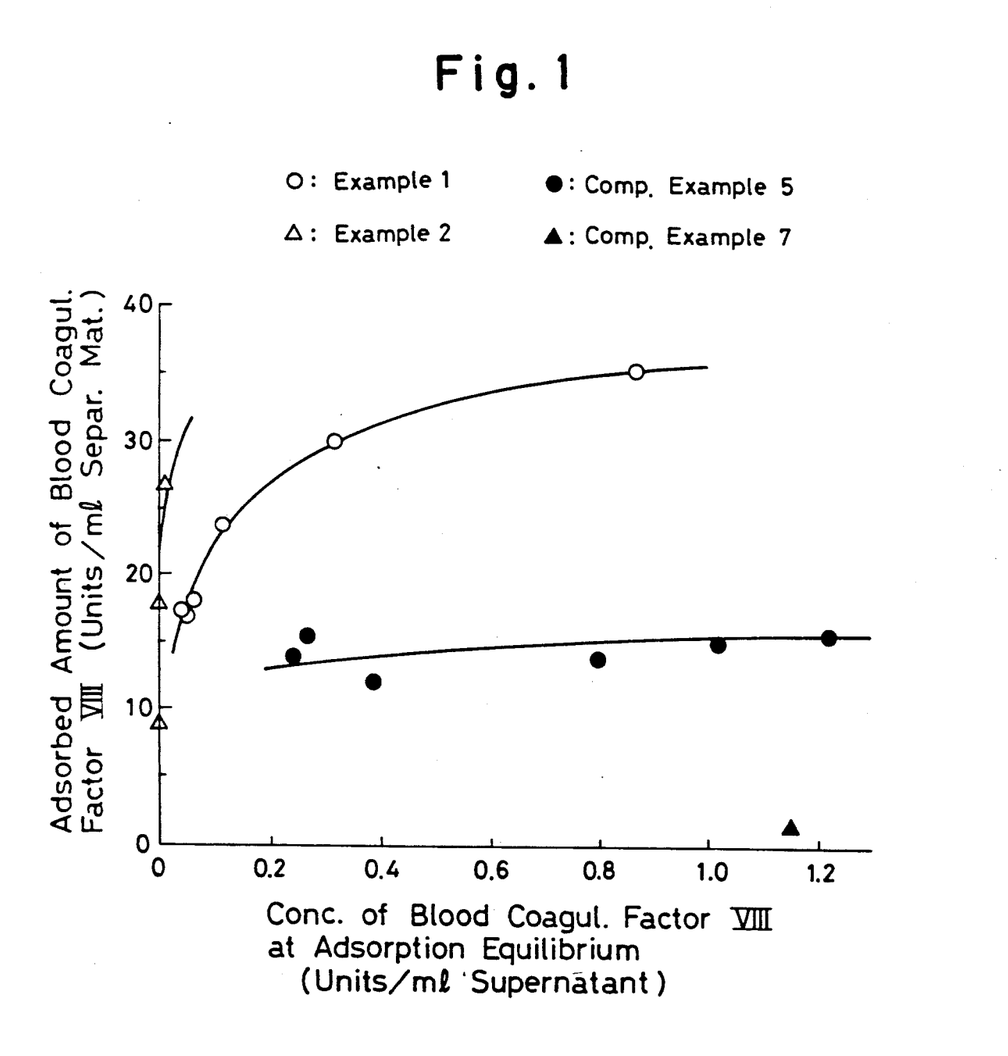
FIG. 1 is a graph showing the experimental results obtained from Examples 1 and 2 and Comparison Examples 5 and 7.

The relationship between the concentration of blood coagulation factor VIII in the supernatant and the amount of adsorption thereof is shown in the graph of FIG. 1.

2-b) Adsorption-Desorption Experiment by Column Method

The separation material product $A_1$ was charged in a glass column having an inner diameter of 3 mm and a length of 40 mm according to normal practice. This column was loaded with 500 μl of the cryoprecipitate solution A by using an injector at room temperature. For this, a flow velocity of 25.5 cm/hr was employed.

While monitoring the effluent liquid by UV (280 nm), the buffer solution A was passed therethrough until no protein had been detected.

Then, the column was loaded with 1 ml of the buffer solution B at room temperature by using an injector to cause desorption. For this, a flow velocity of 85 cm/hr was chosen.

The amount of blood coagulation factor VIII in the effluent passing through the column without being adsorbed on the beads and the amount of blood coagulation factor VIII desorbed from the beads were determined in the same manner as in the preparation of the sample.

The results of the determinations show that 98% of blood coagulation factor VIII had been adsorbed on the separation material $A_1$ and that 99% of the thus adsorbed blood coagulation factor VIII had been recovered (Example 3).

The adsorption rate and the recovery yield of blood coagulation factor VIII were not influenced by incorporating a flow velocity of 170 cm/hr upon adsorption and desorption of blood coagulation factor VIII (Example 4).

From the results of Examples 3 and 4, it is seen that the separation material $A_1$ allows an efficient separation of blood coagulation factor VIII in cryoprecipitate solutions at a high flow rate.

COMPARISON EXAMPLES 1-7

1) Experiments for the Separation of Blood Coagulation Factor VIII

Adsorption experiments were carried out by the batch method in the same manner as in Examples 1 and 2 using each of the separation material products $B_1$–$B_6$ and $B_8$ instead of using the separation material products $A_1$ and $A_2$. The results are summarized also in Table 5. As for Comparison Examples 5 and 7, the relationship between the concentration of blood coagulation factor VIII in the supernatant liquid and the amount of adsorption thereof is plotted in the graph of FIG. 1.

The separation material product $B_8$ was a commercial product EAH-Sepharose 4B (Trademark, a product of an epoxy-activated aminohexylamino-Sepharose of Pharmacia) as such.

As seen from Table 5, the separation material product $A_1$, which is obtained by introducing aminohexylamino radicals up to a ligand concentration of 53 μM/ml separation material into a cross-linked glucomannan bead product GM-$A_1$ having an exclusion limit molecular weight of 1,700,000 and a specific surface area of 3.4 m²/ml separation material with respect to the pores that have diameters of at least 0.1 μm, exhibits an adsorption capacity which becomes greater as the concentration of blood coagulation factor VIII is increased, wherein an adsorption capacity of 35.4 Units per ml of separation

TABLE 5

| Example or Comp. Example | Exp. No. | Separation Material Symbol | Separation Material Amount (μl) | Cryoprecipitate Soln. Symbol | Cryoprecipitate Soln. Amount loaded (μl) | Adsorption Rate (%) | Amount[2] adsorbed (Units/ml sep. mat.) | Conc. in Supernat. (Units/ml supernat.) |
|---|---|---|---|---|---|---|---|---|
| Example 1 | 1 | $A_1$ | 50 | B | 700 | 95.9 | 16.8 | 0.051 |
| | 2 | $A_1$ | 50 | C | 700 | 95.2 | 18.5 | 0.067 |
| | 3 | $A_1$ | 50 | D | 700 | 93.3 | 23.6 | 0.121 |
| | 4 | $A_1$ | 50 | B | 700 | 96.5 | 16.9 | 0.044 |
| | 5 | $A_1$ | 50[3] | B | 700 | 74.4 | 29.9[3] | 0.320 |
| | 6 | $A_1$ | 50[3] | B | 700 | 30.6 | 35.4[3] | 0.868 |
| Example 2 | 7 | $A_2$ | 50 | E | 700 | 98.5 | 8.9 | 0.010 |
| | 8 | $A_2$ | 50[4] | E | 700 | 98.9 | 17.9[4] | 0.007 |
| | 9 | $A_2$ | 50[4] | E | 700 | 98.5 | 26.9[4] | 0.010 |
| Com. Ex. 1 | 10 | $B_1$ | 40 | B | 700 | 82.2 | 18.0 | 0.222 |
| | 11 | $B_1$ | 40 | C | 700 | 77.5 | 18.9 | 0.313 |
| | 12 | $B_1$ | 40 | D | 700 | 64.0 | 21.3 | 0.652 |
| Com. Ex. 2 | 13 | $B_4$ | 40 | B | 700 | 74.4 | 16.3 | 0.320 |
| | 14 | $B_4$ | 40 | C | 700 | 74.7 | 18.2 | 0.352 |
| | 15 | $B_4$ | 40 | D | 700 | 65.3 | 20.7 | 0.628 |
| Com. Ex. 3 | 16 | $B_2$ | 40 | A | 800 | 83.5 | 15.0 | 0.149 |
| Com. Ex. 4 | 17 | $B_3$ | 40 | A | 800 | 82.0 | 14.8 | 0.162 |
| Com. Ex. 5 | 18 | $B_5$ | 50 | B | 700 | 80.6 | 14.1 | 0.243 |
| | 19 | $B_5$ | 50 | C | 700 | 80.7 | 15.7 | 0.268 |
| | 20 | $B_5$ | 50 | D | 700 | 55.8 | 14.1 | 0.800 |
| | 21 | $B_5$ | 50 | B | 700 | 68.7 | 12.0 | 0.391 |
| | 22 | $B_5$ | 50[5] | B | 700 | 18.7 | 15.3[5] | 1.02 |
| | 23 | $B_5$ | 50[5] | B | 700 | 2.1 | 15.7[5] | 1.22 |
| Com. Ex. 6 | 24 | $B_6$ | 50 | B | 700 | 67.7 | 11.8 | 0.404 |
| Com. Ex. 7 | 25 | $B_8$[6] | 50 | B | 700 | 7.9 | 1.4 | 1.15 |

Notes:
[1]Comparison of adsorption rate values of blood coagulation factor VIII with each other is permitted, but comparison of adsorption amount values is not able due to inconsistency of the blood coagulation factor VIII in the supernatant.
[2]Concentration in Units of blood coagulation factor VIII per ml of separation material.
[3]Separation Material $A_1$ used in Experiment No. 4 was recovered and used in Exp. No. 5. Similarly, Separation Material $A_1$ used in Exp. No. 5 was used in Exp. No. 6. Amount of adsorption of blood coagulation factor VIII given represents the over-all value.
[4]As noted in 3 above.
[5]As noted in 3 above.
[6]Separation material $B_8$ was EAH-Sepharose 4B (a commercial product of epoxy-activated aminohexylaminated Sepharose from Pharmacia).

material was observed at a blood coagulation factor VIII concentration in the supernatant of 0.868 Units per ml of the solution (Example 1). Thus, using the separation material product $A_1$, blood coagulation factor VIII contained in raw substances can easily and efficiently be recovered by first causing blood coagulation factor VIII to adsorb on this separation material and then eluting the thus adsorbed coagulation factor from the separation material using a desorption buffer solution having no content of blood coagulation factor VIII to effect desorption thereof.

It is also seen that the separation material product $A_2$, which is obtained by introducing aminohexylamino radicals into a porous cross-linked glucomannan product $GM-A_2$ having an exclusion limit molecular weight of 3,000,000, up to a ligand concentration of 71 $\mu M/ml$ separation material and a specific surface area, with respect to pores having diameters of at least 0.1 $\mu m$, of 4.3 $m^2/ml$ separation material, exhibited a greater adsorption capacity than the separation material product $A_1$ (Example 2).

On the other hand, the separation material products $B_1-B_6$ and $B_8$ showed lower adsorption capacities for blood coagulation factor VIII (Comparison Examples 1-7).

EXAMPLES 5-8, COMPARISON EXAMPLES 8-12

Using the separation material products $A_1$ (Example 5), $A_2$ (Example 6), $A_3$ (Example 7) and $A_4$ (Example 8) and the separation material products $B_1$ (Comparison Example 8), $B_4$ (Comparison Example 9), $B_5$ (Comparison Example 10), $B_6$ (Comparison Example 11) and $B_7$ (Comparison Example 12), a series of adsorption experiments by the batch method were carried out in the same manner as in Example 1 and 2, in order to find out the relationship between the concentration of blood coagulation factor VIII in the supernatant and the amount of adsorption of blood coagulation factor per ml of separation material. The typical example of the relationship between the blood coagulation factor concentration in the supernatant and the amount of adsorption thereof is shown in FIG. 2.

EXAMPLES 9-12, COMPARISON EXAMPLES 13-15

Comparison of the amount of adsorption of blood coagulation factor VIII was carried out for each separation material product.

Figure 2:
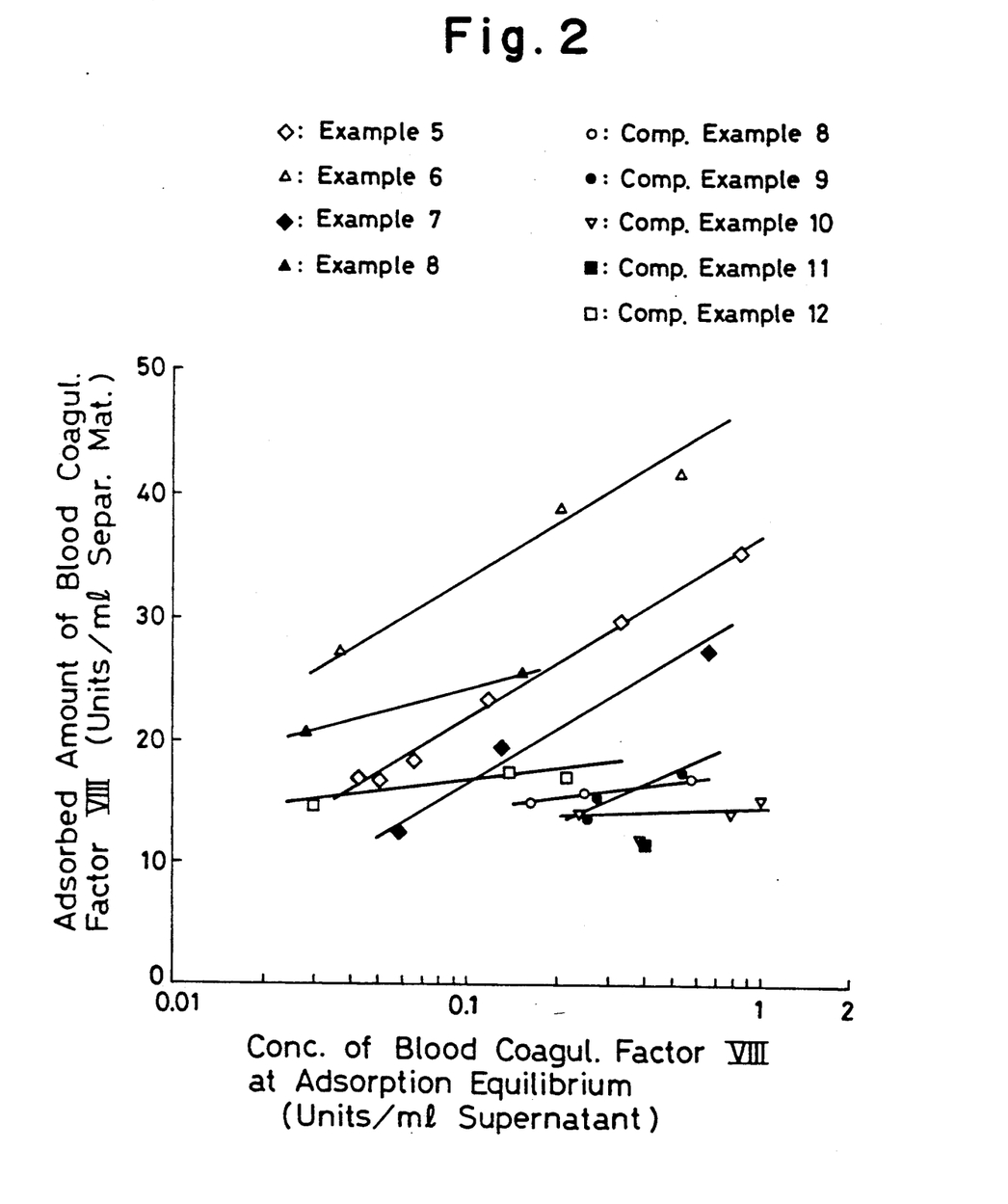
FIG. 2 is a graph showing the experimental results obtained from Examples 5-8 and Comparison Examples 8-12.

The amount of adsorption of blood coagulation factor VIII for each separation material at a concentration of the blood coagulation factor of 0.5 Units per milliliter was calculated from the graph of FIG. 2. The values for Example 8 and for Comparison Example 12 were obtained from curves in the graph by extrapolation.

Figure 3:
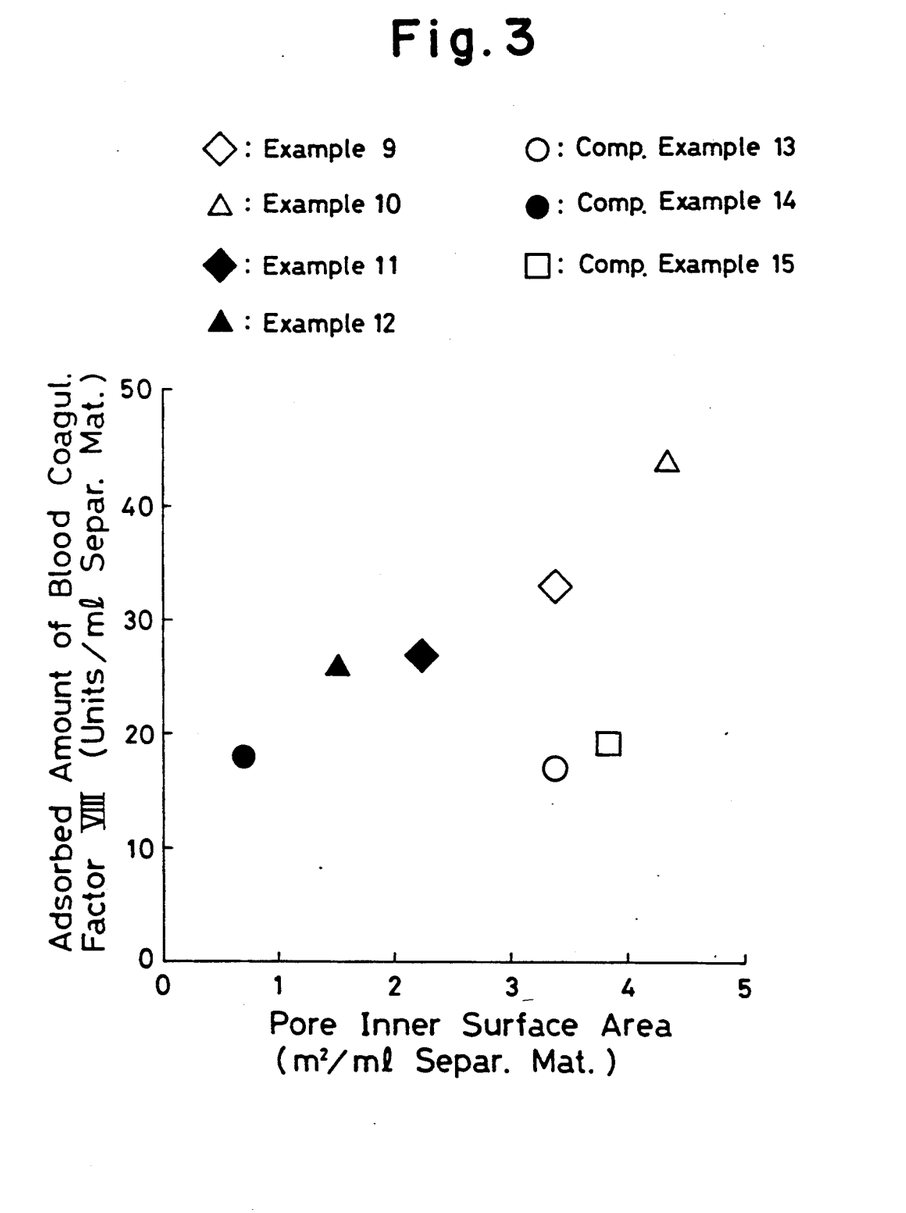
FIG. 3 is a graph showing the experimental results obtained in Examples 9-12 and Comparison Examples 13-15.

The relationship between the amount of adsorption of blood coagulation factor VIII for each of the separation materials and the specific surface area with respect to pores having diameters of at least 0.1 $\mu m$ for the separation material is shown in the graph of FIG. 3. In FIG. 3, the specific surface area is denoted on the abscissa as "pore inner surface area".

Example 9 provides for use of the separation material $A_1$, Example 10 for the separation material $A_2$, Example 11 for the separation material $A_3$, Example 12 for the separation material $A_4$, Comparison Example 13 for the separation material $B_1$, Comparison Example 14 for the seapration material $B_4$ and Comparison Example 15 for the separation material $B_7$ respectively.

EXAMPLE 13

1) Preparation of a Solution of Limited Degradation Product of Collagen IV

Collagen IV was dissolved in 0.1M acetic acid (pH 2.9) to prepare a solution of a concentration of 4 mg/ml. Here, the dissolution was effected carefully with a revolving rotor for a period of 3-4 hours in a plastic sample tube so as not to cause bubbling. Thereto was added of a solution of pepsin of 1 mg per milliliter of sodium acetate buffer solution (pH 5.5) in an amount of 80 $\mu l$ per 1 milliliter of the collagen solution and digestion of the collagen was caused for a predetermined period of time at 37° C. Then, the pH of the solution was adjusted to 7-8 by adding 140 $\mu l$ of 1M tris solution. Thereafter, in order to reduce the decomposed limited degradation product of collagen, 136 $\mu l$ of 0.1M dithiothreitol solution (dissolved in 100 mM phosphate buffer solution containing 5 mM EDTA; pH 6.0) were added thereto to conduct the reaction for 30 minutes at 37° C. Then, 87 $\mu l$ of 0.5M monoiodoacetamide (dissolved in 275 mM tris-hydrochloride solution; pH 8.8) were added thereto in order to prevent the re-combination by —SH group and the reaction was conducted at 30° C. for 10 minutes. The resulting solution was dialyzed under the condition of 4° C. against a buffer solution of 0.1M $NaHCO_3$-0.5M NaCl of pH 8.0, in order to remove the unreacted materials and low-molecular weight amino acids in the solution, whereby a solution of the limited degradation product of collagen IV was obtained.

2) Preparation of Tresylated Glucomannan Beads 0.4 g of dried cross-linked glucomannan beads having an exclusion limit molecular weight of $2 \times 10^6$ determined as into the case of $GM-A_1$ was introduced in a mixed liquid of 3 ml of acetone and 150 $\mu l$ of pyridine. A sample tube filled with this reaction liquid was briefly shaken and thereto were added 100 $\mu l$ of tresyl chloride as the activating agent. The reaction was conducted for 10 minutes while shaking the sample tube. After the reaction, the tresylated glucomannan beads were separated from the reaction medium by filtration under a negative pressure. The beads were washed a mixed solution of acetone and 5 mM hydrochloric acid in a volume ratio of 70:30, a mixed solution of acetone and 5 mM hydrochloric acid in a volume ratio of 30:70 and finally with 1 mM hydrochloric acid in this sequence. The tresylated glucomannan beads so prepared were stored in 1 mM hydrochloric acid at 4° C. (this is denoted hereinafter as tresylated GM/1 mM HCl).

3) Production of Separation Material

The limited degradation product of collagen IV was introduced into the tresylated glucomannan beads in the manner given below to produce a separation material.

An adequate amount of the suspension of tresylated GM/1 mM HCl was placed in a 10 ml sample tube and was subjected to a centrifugation. The supernatant of the centrifugation was pipetted out so as to adjust the volume ratio of the tresylated glucomannan beads to the supernatant to be 1:1. The tresylated GM/1 mM HCl held in a separated state by the centrifugation was shaken to form a uniform suspension of the beads and 1 milliliter of the so formed uniform suspension was quickly pipetted out and transferred into a 3 ml Serum-tube (Trademark, a product of Sumitomo Chemical Co.). After centrifugation, almost all the supernatant was removed by pipetting out using a Pasteur pipette.

To 0.5 ml of the tresylated glucomannan beads remaining in the Serumtube, 1 ml of the solution of limited degradation product of collagen IV was added in a Vortex mixer while shaking. During the first few minutes, the shaking of the reaction mixture was continued as such. Then, the reaction of the mixture was conducted in an incubator for 3 hours at 30° C. After 3 hours, the reaction mixture was filtered on a 3G2 glass filter to separate the solids. The thus obtained separation material $A_5$ was washed with 0.1M $NaHCO_3$–0.5M NaCl buffer solution (pH 8.0) and with 1M NaCl solution. In order to block up the tresyl groups remaining unreacted, the separation material was immersed in 0.1M tris-hydrochloride-0.5M NaCl buffer solution (pH 8.0) at 4° C.

The specific surface area with respect to pores with diameters of at least 0.1 μm as observed in the same manner as in the separation material $A_1$ was 3.0 m²/ml separation material.

4) Experiment of Adsorption of Blood Coagulation Factor VIII

The separation material $A_5$ was charged by normal practice into a glass column having an inner diameter of 3 mm and a length of 40 mm. This column was loaded with 500 μl of the cryoprecipitate solution A using an injector and then buffer solution A (20 mM tris-hydochloride, 1 mM $CaCl_2$, 100 mM NaCl; pH 7.4) was passed through the column at a flow velocity of 0.01 ml/min., while monitoring the effluent liquid by a UV (280 nm), until no protein had been detected. The concentration of blood coagulation factor VIII in the effluent was determined using Testteam® F VIII and the amount of blood coagulation factor VIII adsorbed on the separation material $A_5$ was calculated from the difference between this analysis value and the loaded amount thereof. It was determined that 1.33 Units of blood coagulation factor VIII were absorbed per 1 ml of the separation material $A_5$. The ratio of the adsorbed amount of blood coagulation factor VIII on the separation material $A_5$ to the loaded amount thereof was determined to be 53%.

We claim:

1. A separation material for separating and recovering a blood coagulation factor, comprising a porous matrix derived from glucomannan and having linked thereon one or more ligands, each ligand consisting of a radical exhibiting an affinity to the blood coagulation factor to be recovered, said matrix having a specific surface area of at least 1.5 m² per milliliter of the separation material with respect to pores having diameters of at least 0.1 μm and said matrix being derived from a porous particulate material having an exclusion limit molecular weight of at least $1.5 \times 10^6$ as determined with polyethylene glycol.

2. A separation material for separating and recovering a blood coagulation factor as claimed in claim 1, wherein the blood coagulation factor to be recovered is blood coagulation factor VIII or a complex thereof with von Willebrand factor.

3. A separation material for separating and recovering a blood coagulation factor as claimed in claim 1, wherein the ligand consists of one or more substances selected from the group consisting of collagens, monoclonal antibodies and substances having a group represented by the following general formula (I)

in which $R^1$ and $R^2$ each represent a hydrogen atom or a lower alkyl group and may be identical with or different from each other, l is a number of 0 or 1, m is an integer of 3–8, n equals to 0 or 1 and p is an integer of 0–5.

4. A separation material for separating and recovering a blood coagulation factor as claimed in claim 1, wherein the particulate material has an exclusion limit molecular weight in the range of $2 \times 10^6$ to $5 \times 10^6$ as determined with polyethylene glycol.

5. A separation material for separating and recovering a blood coagulation factor as claimed in claim 1, wherein said glucomannan is konjakmannan.

6. A separation material for separating and recovering a blood coagulation factor as claimed in claim 1, wherein said matrix has a specific surface area of at least 3 m² per milliliter of separation material with respect to pores having diameters of at least 0.1 μm.

7. A separation material for separating and recovering a blood coagulation factor as claimed in claim 1, wherein said radical is selected from the group consisting of an aminobutylamino radical, an aminohexylamino radical and an aminobutylcarbamylbutylamino radical.

8. A process for preparing a separation material for separating and recovering a blood coagulation factor, comprising the steps of subjecting a porous particulate material derived from glucomannan and having an exclusion limit molecular weight of at least $1.5 \times 10^6$ to activation by 1,1'-carbonyldiimidazolating, tresylating, carbodiimidizing, thiopropylating, epoxidizing, bromocyanizing or formylating using a corresponding activating agent and reacting the so activated porous particulate material with one or more substances which exhibit after being linked as a ligand on the porous particulate material, an affinity to the blood coagulation factor to be recovered, so as to form a porous matrix having a specific surface area of at least 1.5 m² per milliliter of the porous particulate material with respect to pores having diameters of at least 0.1 μm.

9. A process for preparing a separation material for separating and recovering a blood coagulation factor as claimed in claim 8, wherein the particulate material has an exclusion limit molecular weight in the range of $2 \times 10^6$ to $5 \times 10^6$ as determined with polyethylene glycol.

10. A process for preparing a separation material for separating and recovering a blood coagulation factor as claimed in claim 8, wherein said glucomannan is konjakmannan.

11. A process for preparing a separation material for separating and recovering a blood coagulation factor as claimed in claim 8, wherein said matrix has a specific surface area of at least 3 m² per milliliter of separation material with respect to pores having diameters of at least 0.1 μm.

12. A process for preparing a separation material for separating and recovering a blood coagulation factor as claimed in claim 8, wherein said ligand is selected from the group consisting of an aminobutylamino radical, an aminohexylamino radical and an aminobutylcarbamylbutylamino radical.

13. A process for recovering a blood coagulation factor from a blood coagulation factor-containing raw material using a separation material which comprises a porous matrix derived from glucomannan and having linked thereon one or more ligands, each ligand consisting of a radical exhibiting an affinity to the blood coagulation factor to be recovered, said matrix having a specific surface area of at least 1.5 m² per milliliter of the separation material with respect to pores having diameters of at least 0.1 μm and said matrix being derived from a porous particulate material having an exclusion limit molecular weight of at least $1.5 \times 10^6$ as determined with polyethylene glycol, said process comprising the steps of bringing the raw material into contact with the separation material under the use of an adsorption buffer solution and subjecting the resulting separation material containing thus the blood coagulation factor adsorbed thereon to elution by contacting it with an eluent buffer solution to collect the blood coagulation factor.

14. A process for recovering a blood coagulation factor from a blood coagulation factor-containing raw material using a separation material for separating and recovering a blood coagulation factor as claimed in claim 13, wherein the blood coagulation factor to be recovered is blood coagulation factor VIII or a complex thereof with von Willebrand factor.

15. A process for recovering a blood coagulation factor from a blood coagulation factor-containing raw material using a separation material for separating and recovering a blood coagulation factor as claimed in claim 13, wherein the ligand consists of one or more substances selected from the group consisting of collagens, monoclonal antibodies and substances having a group represented by the following general formula (I)

in which $R^1$ and $R^2$ each represent a hydrogen atom or a lower alkyl group and may be identical with or different from each other, l is a number of 0 or 1, m is an integer of 3–8, n equals to 0 or 1 and p is an integer of 0–5.

16. A process for recovering a blood coagulation factor from a blood coagulation factor-containing raw material using a separation material for separating and recovering a blood coagulation factor as claimed in claim 13, wherein the porous matrix has an exclusion limit molecular weight in the range of $2 \times 10^6$ to $5 \times 10^6$ as determined with polyethylene glycol.

17. A process for recovering a blood coagulation factor from a blood coagulation factor-containing raw material using a separation material for separating and recovering a blood coagulation factor as claimed in claim 13, wherein said matrix has a specific surface area of at least 3 m² per milliliter of separation material with respect to pores having diameters of at least 0.1 μm.

18. A process for recovering a blood coagulation factor from a blood coagulation factor-containing raw material using a separation material for separating and recovering a blood coagulation factor as claimed in claim 13, wherein said glucomannan is konjakmannan.

19. A process for recovering a blood coagulation factor from a blood coagulation factor-containing raw material using a separation material for separating and recovering a blood coagulation factor as claimed in claim 13, wherein said ligand is selected from the group consisting of an aminobutylamino radical, an aminohexylamino radical and an aminobutylcarbamylbutylamino radical.

* * * * *

UNITED STATES PATENT AND TRADEMARK OFFICE
CERTIFICATE OF CORRECTION

PATENT NO. : 5,096,593

DATED : March 17, 1992

INVENTOR(S) : Masaaki WAKITA et al

It is certified that error appears in the above-identified patent and that said Letters Patent is hereby corrected as shown below:

On the title page, at item [57], line 10; change "$1.5 \times 1^6$" to ---$1.5 \times 10^6$---.

line 19; after "exhibit" insert a comma.

line 21; change "covered" to ---recovered---.

Column 26, line 42; after "exhibit" insert a comma.

Signed and Sealed this

Tenth Day of August, 1993

Attest:

MICHAEL K. KIRK

*Attesting Officer*     *Acting Commissioner of Patents and Trademarks*